United States Patent [19]

Chao et al.

[11] Patent Number: 5,428,008
[45] Date of Patent: Jun. 27, 1995

[54] THERAPEUTIC COMPOSITION OF MICELLAR STRUCTURES CAPABLE OF PROMOTING HEMOTASIS

[75] Inventors: Francis C. Chao, Newton; Frank H. Liang, Shrewsbury, both of Mass.

[73] Assignee: PRP, Inc., Watertown, Mass.

[21] Appl. No.: 786,056

[22] Filed: Oct. 31, 1991

Related U.S. Application Data

[63] Continuation-in-part of Ser. No. 508,832, Apr. 12, 1990, abandoned, which is a continuation-in-part of Ser. No. 337,916, Apr. 14, 1989, Pat. No. 5,185,160.

[51] Int. Cl.$^6$ .......................... A61K 37/10; C12N 5/00
[52] U.S. Cl. ........................................ 514/8; 424/532; 435/240.2
[58] Field of Search ................ 424/532, 101; 435/236, 435/240.2; 514/8

[56] References Cited

U.S. PATENT DOCUMENTS

| | | | |
|---|---|---|---|
| 4,731,053 | 3/1988 | Hoffman | 604/89 |
| 4,760,131 | 7/1988 | Sundsmo et al. | 530/356 |
| 4,871,488 | 10/1989 | Mannino et al. | 264/4.6 |
| 5,285,160 | 2/1993 | Chao | 424/532 |

FOREIGN PATENT DOCUMENTS 151108 10/1981 Germany.

OTHER PUBLICATIONS

Rybak, M. E., Renzulli, L. A., Bruns, M. J., Cahaly, D. P., "Platelet Glycoproteins IIb and IIIa as a Calcium Channel in Liposomes", Blood, vol. 72, No. 2 (Aug.), 1988, pp. 714–720.

McGill, M., Fugman, D. A., Vittorio, N., Darrow, C., "Platelet membrane vesicles reduced microvascular bleeding times in thrombocytopenic rabbits", J. Lab. Clin. Med. 1987, 109:127–133.

Rybak, M. E., Linden, H., Zimarowski, M. I., Baca, M., Renzulli, L., "The Plateletsome Immune Lysis Assay (PILA) A New Highly Specific Assay for Autoimmune Thrombocytopenia (ITP)", 1982 Platelets and Megakaryocyes Abstract, p. 473a.

Rybak, M. E., Renzulli, L., "A liposome Based Platelet Substitute, The Plateletsome, with Hemostatic Efficacy", 1983 Platelets and Megakaryo-cytes Abstract, p. 473a.

Sie, P., Gillois, M., Boneu, B., Chap, H., Bierme, R., Douste-Blazy, L., "Reconstitution of Liposomes Bearing Platelet Receptors for Human von Willebrand Factor", Biochemical and Biophysical Research Communications, 97:133–138 (Nov. 17, 1980).

Baldassare, J. J., Kahn, R. A., Knipp, M. A., Newman, P. J., "Reconstruction of Platelet Proteins into Phospholipid Vesicles", J. Clin. Invest. 75:35–39 (Jan. 1985).

Parise L. V., Phillips, D. R., "Platelet Membrane Glycoprotein IIb-IIIa Complex Incorporated into Phospholipid Vesicles", The Journal of Biological Chemistry 260:1750–1756 (Feb. 1985).

Zucker, M. B., "Can platelet fragments induced hemostasis?", J. Lab. Clin. Med., 109:111 (1987).

Etemadi, A.-H., "Functional and Orientational Features of Protein Molecules in Reconstituted Lipid Membranes", Advances in Lipid Research 21:281–301 ( ).

Jamieson, G. A., Pepper, D. S., "Membrane Glycoproteins of Blood Platelets", The Circulating Platelet pp. 189–205 (1971).

Marcus, A. M., Safier, L. B., Ullman, H. L., "Functions of Platelet Membranes", The Circulating Platelet pp. 241–259 (1971).

Perry, S., Yankee, R. A., "Transfusion and Preservation", The Circulating Platelet pp. 541–551 (1971).

*Primary Examiner*—Douglas W. Robinson
*Assistant Examiner*—Deborah K. Ware
*Attorney, Agent, or Firm*—Wolf, Greenfield & Sacks

[57] ABSTRACT

A reconstituted platelet membrane vesicle or micellar structure preparation is provided. The preparation, directed at promoting hemostasis, may be prepared from proteins and lipids derived from either synthetic sources or from mammalian platelet membranes. The product may be used for transfusions or may be topically applied. Methods for forming the vesicles or micellar structures and products for storing and dispensing the vesicles or micellar structures also are disclosed.

16 Claims, 5 Drawing Sheets

SDS-PAGE ELECTROPHORESIS OF
THE RECONSTITUTED PLATELET MEMBRANE VESICLES

(REDUCED, COOMASSIE BLUE STAIN)

A: PLATELET GLYCOPROTEINS (GP)
B: RECONSTITUTED MIXTURE (RM) OF PLATELET LIPID EXTRACT + GP
C: SUPERNATANT OF RM AFTER CENTRIFUGATION
D: WASHED (4 TIMES) PELLET OF RM
E: MOLECULAR WEIGHT STANDARD

Fig. 1

IMMUNOBLOTTING OF PLATELET GLYCOPROTEINS
AND RECONSTITUTED PLATELET MEMBRANE VESICLES (PRIMARY ANTIBODY: ANTI-GLYCOCALICIN MoAb)

A: WASHED PELLETS OF RECONSTITUTED PLATELET MEMBRANE VESICLES
B: PLATELET GLYCOPROTEINS

PANEL A: PLATELET GLYCOPROTEINS

PANEL B: PRE-FORMED PLATELET LIPID LYPOSOME + GP

PANEL C: RECONSTITUTED PLATELET MEMBRANE VESICLES

Fig. 4

DOT ASSAY OF RECONSTITUTED PLATELET MEMBRANE VESICLES
AND RED CELL MEMBRANES

ANTI-GLYCOCALICIN MoAb

PANEL A

PANEL B

S1: SUPERNATANT FROM RECONSTITUTED MIXTURE (RM)
Pt1: PELLET FROM RM
S2,3: WASHING SUPERNATANTS
Pt2,3: WASHED PELLETS

Fig. 5

THERAPEUTIC COMPOSITION OF MICELLAR STRUCTURES CAPABLE OF PROMOTING HEMOTASIS

RELATED APPLICATION

This application is a continuation-in-part of U.S. patent application Ser. No. 07/508,832, filed Apr. 12, 1990, now abandoned which in turn is a continuation-in-part of U.S. patent application Ser. No. 07/337,916, filed Apr. 14, 1989, now U.S. Pat. No. 5,185,160, the entire disclosures of which are incorporated herein by reference.

FIELD OF THE INVENTION

This invention relates generally to the field of medicine and particularly to a reconstituted platelet membrane vesicle preparation useful in promoting hemostasis.

BACKGROUND OF THE INVENTION

Lack of adequate numbers and normal function of blood platelets is associated with many disease processes, and can cause debilitating and life threatening blood loss. Thus far, the only effective treatment for these patients has been to transfuse them with donated blood products containing large numbers of viable platelets. This treatment, however, is associated with various problems of supply and safety. Platelets are fragile, and should be separated from whole blood within eight hours. After collection donated platelets have at most only a several day lifespan, after which the platelets are discarded as "outdated." It may require as many as ten donors to obtain a sufficient quantity of platelets for a single transfusion to an adult patient. A large supply of donated blood is required to sustain each patient needing platelet replacement therapy. Because of the short platelet shelf life, and the difficulty of obtaining sufficient donated blood from which to isolate platelets, shortages of fresh platelets are common, with dire consequences for afflicted patients.

The transfusion of fresh platelets has raised safety issues. Infected donor platelets have transmitted hepatitis and AIDS. While improved tests for these viruses have greatly lowered the transmission rate, the tests still cannot ensure complete detection of all infected blood products.

Given the problems of platelet availability and safety, a safe and readily available transfusable platelet substitute with hemostatic function would provide substantial benefits for many patients. Producing a platelet substitute which preserves the hemostatic functions of the native platelet has been difficult due to the complex nature of the platelet. The platelet membrane has many components including lipids, proteins, and carbohydrates, all of which may be involved in the hemostatic function of the cell.

Although investigators have formed reconstituted vesicles carrying platelet glycoproteins, such reconstituted vesicles have been for use as basic research models, and did not involve evaluation of the hemostatic properties of the reconstituted membranes. Several recent publications have reported combining glycoproteins from platelets with purified phospholipids for the purpose of studying the function of platelet proteins in simplified artificial membrane structures. Partially purified platelet glycoproteins were inserted into simple phosphatidylcholine or phosphatidylcholine-phosphatidylserine liposomes by Sie et al. (1980), Parise and Phillips (1985), Baldasarre et al. (1985), and Rybak et al. (1988), none of which described using the products in animals.

SUMMARY OF THE INVENTION

The invention provides products and methods relating to therapeutic material corresponding to components of platelet membranes, in the form of reconstituted platelet membrane vesicles. Reconstituted platelet membrane vesicles are micellar structures formed from at least one type of phospholipid, into which is inserted at least one type of glycoprotein typically found in platelet membranes and involved in hemostasis. The vesicles of the invention have the ability to promote hemostasis and may be used to treat subjects lacking adequate hemostatic function or as a supplement in normal subjects. They may be used, for example, prophylactically, in wound healing or during medical procedures, and they may be formulated as transfusion material or in topical preparations.

Thus, according to one aspect of the invention, a therapeutic material is provided, that is, a pharmaceutically acceptable sterile preparation of reconstituted platelet membrane vesicles capable of promoting hemostasis. Preferably, sufficient glycoprotein involved in hemostasis is associated with the vesicles so that the vesicles are pharmaceutically effective when introduced intravenously. Most preferably, the vesicles include a phospholipid having procoagulant activity. In one preferred embodiment, the vesicles contain glycoprotein and phospholipid in relative amounts on the order of the glycoprotein: phospholipid ratio present in human platelet membrane. The vesicles optionally may contain a therapeutic substance, such as a vasoconstrictive agent (e.g., seratonin).

The foregoing materials are administered to patients in order to promote hemostasis.

According to another aspect of the invention, a method of preparing a therapeutic material is provided. A phospholipid preparation is combined with a glycoprotein preparation, and mixed under conditions to form a sterile preparation of reconstituted membrane vesicles that is capable of promoting hemostasis. Methods are also provided for optimizing the phospholipid composition to yield vesicles with maximal incorporation of glycoprotein and optimize the glycoprotein: phospholipid ratio to maximize hemostatic efficacy.

According to yet another aspect of the invention, the vesicles are formulated from source material other than fresh human platelets, which typically are in short supply. The phospholipids may be derived from fresh or outdated human platelet membrane, from other cell membranes, from non-human cell membrane sources or even synthetically. The glycoproteins may be derived from fresh or outdated platelet membranes, human or non-human. The glycoproteins also may be products of genetic engineering.

Still another aspect of the invention involves containers that permit long-term storage of the starting materials for forming the membrane vesicles and containers that permit on-site reconstitution of the membrane vesicles. Such containers include at least a first sealed chamber with a chamber wall having a preselected amount of a sterile dried phospholipid preparation coated thereon. A glycoprotein preparation, preferably in solution, may be introduced into that chamber and vortexed to create the membrane vesicles of the invention. The container can include a second sealed chamber in which is stored the glycoprotein preparation, and further may include means for introducing the glycoprotein preparation into the first sealed chamber (e.g., a penetrable or frangible membrane separating the two chambers. The phospholipid preparation and glycoprotein preparation further can be supplied in preselected amounts in containers assembled into kits.

Thus, it is among the objects of the invention to create a platelet membrane vesicle substitute having a hemostatic capability.

Another object of the invention is to create a platelet membrane vesicle substitute that can be manufactured from source material other than fresh human platelets.

Still another object of the invention is to provide a platelet substitute capable of long-term storage in a dry, unreconstituted state and that is virus free.

These and other objects will be more apparent with reference to the detailed description of the invention which follows.

DETAILED DESCRIPTION OF THE INVENTION

The invention involves the discovery that hemostasis is facilitated by treating a subject with platelet membrane vesicles that have been reconstituted from a glycoprotein preparation and a phospholipid preparation. Hemostasis means the control of blood loss from blood vessels. The hemostatic capability of the reconstituted platelet membrane vesicle is influenced by several interdependent variables, including the type of glycoproteins in the membranes, the types and relative proportions of the membrane phospholipids and the relative amounts of glycoproteins with respect to phospholipids.

The glycoprotein composition of the reconstituted platelet membrane vesicles is central to the essential hemostatic function. As used herein, the terms glycoprotein and glycoprotein preparations are intended to mean glycoproteins associated with platelet membranes and having a hemostatic function. Such glycoproteins can be isolated from platelet membranes or can be the product of genetic engineering. While a preferred source for the glycoprotein isolations is either fresh or outdated human platelets, membranes from platelets of nonhuman mammalian species may also be used, including cows, horse or swine. Glycoproteins may be isolated from human or nonhuman mammalian platelets by first centrifuging and washing blood platelets. The platelet-containing pellet then can be resuspended in a Triton detergent solution which is centrifuged over sucrose cushions to separate the proteins. The crude glycoprotein isolate then can be purified by affinity chromatography over a wheat germ lectin column, eluted with N-acetyl-glucosamine.

A mixed glycoprotein solution isolated from platelet membranes can be used in the preparation of the reconstituted platelet membrane vesicles of the invention. In certain embodiments of the invention, the reconstituted platelet membrane vesicles are prepared from glycoprotein solutions which are either enriched in or deficient in particular glycoproteins. Preparing the reconstituted platelet membrane vesicles with different glycoprotein composition will effect the hemostatic properties of the final product because of the different roles the various platelet membrane glycoproteins play in the hemostatic functions of the platelets. For example, GP Ib is believed to contain the receptor site for thrombin and to mediate platelet adhesion. Glycoprotein Ib (GP Ib) may function for maintaining the integrity and normal physiology of the blood vessel endothelium, and thus prevents blood leakage from blood vessels. The glycoprotein complex IIb/IIIa (GP IIb/IIIa) functions as a fibrinogen receptor, necessary for platelet aggregation as occurs when a blood clot forms. Thus, vesicles can be formed which mediate distinct hemostatic reactions.

As the functions of different glycoproteins become clarified, the glycoprotein composition of the reconstituted platelet membrane vesicles of the invention can be selected to particularly address different clinical needs. In one example of this concept, a reconstituted platelet membrane preparation can be tailored to have a selected ability to adhere to blood vessels which have damaged endothelium, a function in which GPIb is thought to be involved. As a test system, a length of umbilical vessel is swabbed on its interior surface for half of its length, removing the endothelial cells. Platelet membrane vesicle adhesion can be measured by filling the vessel with a solution of radiolabelled platelet membrane vesicles, allowing adhesion, washing away non-adhered vesicles, and measuring the radiolabel associated with adhered vesicles. This test system can be used to select a glycoprotein composition for platelet membrane vesicles which demonstrates a desired ability to adhere to damaged blood vessel walls.

Thus, in one preferred embodiment of the invention, the reconstituted platelet membrane vesicles are prepared with a glycoprotein preparation which consists essentially of glycoprotein Ib or which is a mixture enriched in glycoprotein Ib. In this embodiment, the glycoprotein preparation can be substantially free of glycoprotein IIb/IIIa complex, yet still have pharmacologic utility.

It will be recognized by one of ordinary skill in the art that molecules or adhesive proteins in other species may be identified that are substantially the same in structure and/or function to the particular glycoproteins discussed herein, but are differently named. Likewise, derivatives of the glycoproteins discussed herein that perform the same or substantially the same biologic function may exist, such as by recombinant technology or by protein chemistry. Such molecules are specifically intended to be covered by the appended claims.

The platelet membrane vesicles of the invention may also contain other proteins that are normally found in platelet membranes. Such proteins include actin and actin-binding protein, which are believed to play a role in proper association of glycoproteins with the membrane.

The lipid composition of the reconstituted platelet membrane vesicles of the invention also is important in achieving hemostatic function. This lipid composition, in particular, the phospholipid composition of the membrane, is believed to affect both the function and the level of incorporation of glycoproteins within the membrane. The phospholipids may themselves have procoagulant activity, thereby enhancing the hemostatic capability of the vesicles when present. For example, phosphatidylserine and phosphatidylethanolanine are believed to have procoagulant activity.

The lipids for the membranes may be derived from fresh or outdated human platelet membranes, from other blood cell membranes, from nonhuman mammalian platelet membranes or from other lipid sources. Particular phospholipid compositions can be prepared by mixing preparations of single purified phospholipids in different amounts.

To prepare the phospholipids from blood samples, platelets can be separated from other blood components by centrifugation. The intact platelets can be disrupted by repeated freezing and thawing. Phospholipids then can be extracted from the platelet membranes using solvent systems and then recovered by drying the lipid-containing solvent. A preferred solvent system is hexane-isopropanol.

The selection and relative amounts of the different phospholipids in the reconstituted platelet membrane vesicles influence the incorporation of glycoproteins within these vesicles. One preferred composition substantially duplicates the phospholipid composition of human platelet membranes. In certain applications, different phospholipid compositions may be found to be preferable. In any case, the phospholipid composition should be selected to promote sufficient glycoprotein incorporation to allow hemostatic capability. It is preferred that the phospholipid composition be such that when glycoproteins are added to the phospholipid preparation under conditions to promote the formation of microvesicles such as those described in the examples below, and where the glycoprotein to phospholipid ratio of starting materials is 1:10 (wt/wt) or less, at least 80% of the added glycoprotein is incorporated into the resultant membrane vesicles.

The ratio of glycoprotein to phospholipids in the membrane vesicles, as mentioned, is related to the hemostatic function of the product of the invention. In a normal human platelet membrane, the protein content is approximately twice that of the phospholipid content by weight. Since the glycoprotein forms about 20–30% of the total protein of the human platelet membrane, the glycoprotein to phospholipid ratio by weight in the human platelet is approximately 2–3:5. In one preferred embodiment of the product of the invention, this ratio is replicated. Since glycoprotein GPIb forms about 5% of the total protein of human platelet membrane, the GPIb content is about 10% of the phospholipid content by weight. Thus, in another preferred embodiment, the vesicles of the invention duplicate this ratio. Generally, the vesicles have enough of a particular glycoprotein associated therewith to achieve the therapeutic effect that the glycoprotein is responsible for. Other embodiments include vesicles with a glycoprotein:phospholipid ratio of 1:20 or greater and vesicles with a GPIb:phospholipid ratio of 1:50 or greater. The optimal amounts may be calculated according to the methods described below.

Other aspects of the invention also contribute to the hemostatic function of the product. For example, therapeutic agents may be associated with the vesicles. In one embodiment of the invention, the reconstituted platelet membrane vesicles may contain therapeutic substances entrapped within the lumina of the individual vesicles to be released when the vesicles rupture as they are involved in hemostatic reactions at bleeding sites. In another embodiment, the therapeutic agent is incorporated into the membrane. Therapeutic substances as used herein refer to substances which effect a medically desirable result when administered to a subject. The therapeutic substances can encompass many pharmaceutical products including vasoconstrictive agents such as seratonin, other biogenic amines, anti-cancer drugs, or antibiotics.

The reconstituted platelet membrane vesicles of the invention are prepared by combining a phospholipid extract or mixture as described above with glycoproteins in solution. The phospholipid preparation can be in the form of a lipidic gel. To form a lipidic gel, dried phospholipids are resuspended in ether, to which is added an aqueous detergent solution. After sonication, the ether is removed by drying, after which the lipidic gel is ready to be combined with a glycoprotein solution. The preferred method of preparing the phospholipids is to dry a phospholipid extract onto the wall of a vessel to which can then be directly added a glycoprotein solution.

The components of the platelet membrane vesicles can be stored for prolonged periods of time in a dried state. Prior to reconstitution, a dried glycoprotein can be solubilized and added to a dried phospholipid preparation. The combination is vortexed for a recommended period of time, which causes the formation of vesicles with incorporated glycoproteins.

One aspect of the invention is a method by which the glycoprotein phospholipid ratio of the reconstituted platelet membrane vesicles can be optimized to yield membrane vesicles with maximal hemostatic efficacy. This method starts by producing batches of reconstituted platelet membrane vesicles with different glycoprotein to phospholipid ratios. This step is accomplished by adding varying amounts of glycoprotein solution to a fixed quantity of dried phospholipid and then forming platelet microvesicles by the method detailed below. (The batches also may be formed by selecting different reconstitution conditions or by varying phospholipid composition to affect glycoprotein incorporation.) The hemostatic efficacy of the batches is measured as described below. Hemostatic efficacy refers to the ability to facilitate hemostasis. For an intravascular treatment, the hemostatic efficacy is defined as a shortening of bleeding time in thrombocytopenic subjects which persists for at least one hour after the intravascular treatment. The optimized glycoprotein to phospholipid ratio is that of the preparation which yields the highest measured hemostatic efficacy.

The phospholipid composition of the reconstituted platelet membrane vesicle may also be optimized. In such a case, batches of reconstituted platelet membrane vesicles with different phospholipid compositions are produced to which are added the same amount of a glycoprotein solution. The preferred phospholipid composition is that of the preparation which incorporates a percentage of glycoproteins that facilitates maximaized hemostatic efficacy.

The reconstituted platelet membrane vesicles of the invention have numerous advantages over the prior art material. In contrast to the severely limited supply of fresh platelets, the reconstituted platelet membrane vesicles can be made from sources which are not in short supply. The potential for obtaining the components for manufacturing the products of the invention from outdated human, nonhuman, or genetically engineered materials will ensure that the product can be made available in large supply and potentially at reasonable cost.

A major advantage of the reconstituted platelet membrane vesicles is the potential for long term storage of the materials prior to reconstitution, which can even be performed when and where the final product is needed. The dried components for making the vesicles can be stored for long periods of time and as such, can be available for ready use in many situations for which availability of fresh platelet material has been limited. These situations include use in the field for various medical situations without recourse to either a steady source of blood donors or to sophisticated blood processing or storage apparatus. Examples of such situations include military operations, ambulatory medical units, emergency and disaster situations, rural medical centers, and veterinary practices. The combination of unlimited supply of the precursors and of storage in dried form for shipping and maintenance for long periods of time, results in a platelet replacement product which can be made available to medical practitioners in many situations and in many areas of the world which were previously denied access to platelet products.

An important result of the process of the invention is that the vesicular membrane product is virus free. Viral contamination, particularly with the hepatitis and the human immunodeficiency viruses, is a significant risk factor in treating patients with fresh platelets. The product of the invention may be produced from nonhuman sources; this precludes contamination of the source material with infectious human virus particles. Even if produced from human starting materials, virus particles do not to survive the extractions and isolation procedures of the invention.

A further advantage of the invention is the consistency of the platelet replacement product. Fresh platelet transfusions have variable clinical efficacy due to their derivation from heterogeneous donor material and often differing isolation procedures. The product of the invention, in contrast, will be produced with specified glycoprotein and phospholipid composition and with predictable hemostatic function. The potential for optimizing the concentrations and compositions of glycoproteins and phospholipids of the product of the invention means that different concentrations of the components can be selected to produce reconstituted platelet membrane vesicles with particularly desired hemostatic capability.

The preparation contains no free serotonin which is usually present in normal platelet preparations. This characteristic of the reconstituted platelet membrane vesicles is desirable since free serotonin causes painful vasospasm during transfusions.

The product of the invention can be of clinical utility in different subjects. The term "subjects" refers to mammals and may include, but is not limited to humans, nonhuman primates, dogs, cats and horses.

The product is given to subjects in pharmaceutically effective amounts. A pharmaceutically effective amount is a dosage of the product sufficient to provide a medically desirable result. The pharmaceutically effective amount of the reconstituted platelet membrane vesicles of the present invention will vary with the particular condition being treated, the age and physical condition of the subject being treated, the severity of the condition, the duration of treatment, the nature of concurrent therapy, the specific route of administration (e.g. intravascular or topical) and like factors within the knowledge and expertise of the attending physician.

The membrane vesicles are to be formulated into a pharmaceutically acceptable preparation. A pharmaceutically acceptable preparation is a composition which is relatively nontoxic and innocuous to a patient at concentrations consistent with effective activity of the carrier ingredient, so that any side effects ascribable to the carrier do not vitiate the beneficial effects of the active ingredient. In addition, the carrier diluent or excipient must be compatible with the other ingredients of the formulation. Nontoxic is intended to include substantially nontoxic, e.g. the agents may have a minimal level of toxicity which does not cause a significant harm to the patient. The preparation is intended to be sterile. By sterile preparation, it is meant a preparation which is free of detectable microorganisms, including bacteria, viruses, fungi and protozoa.

The vesicles of the invention may be used diagnostically or as a part of a research protocol. For example, the reconstituted platelet membrane vesicles can be used to ascertain the location of either blood loss or of sequestration of the unused vesicles. For this embodiment, the membrane vesicles could be labeled for imaging, either by radioactive tags or by encasement of imagable substances such as fluoroscopically visible dyes. The site of the vesicles within the treated subject, as shown by the imaging process, would indicate areas of either intravascular thrombosis or of sequestration, which might be clinically useful information. The selection of particular glycoproteins involved in distinct hemostatic reactions further enhances the usefulness of the vesicles of the invention as a diagnostic tool.

An intended use of the product of the invention is for treating a subject with deficits in hemostatic function. A preferred method of administration of the product is by the intravascular route. Intravascular administration refers to the introduction of the product into a blood vessel, either into a vein or into an artery.

The solution preferably is an isotonic solution of sodium chloride. Where desirable, the solution may also contain plasma, buffers, stabilizers, or therapeutic substances, as well as other medically acceptable additives. The reconstituted platelet membrane vesicles may also be prepared as an additive to other blood products, fluid replacements, or intravenously administered medicaments.

The product for intravascular use may be supplied either as a solution, or compartmentalized for combination by the health care worker. When supplied as a solution, the product may be sterilly packaged in bottles or bags suitable for connection to an intravenous set, or may be supplied in a bottle adapted for access with a syringe.

The product may advantageously be supplied in dry form, to be reconstituted and solubilized at the time of intended use. In such embodiments, the sterile dried phospholipid may be stored within one evacuated syringe-accessible bottle, and a glycoprotein solution within another sterile bottle. For use, the glycoprotein solution is drawn into a syringe, which is then used to expel the solution into the bottle containing the phospholipid. After reconstituting the platelet membrane vesicles by vortexing the bottle, the solution is redrawn into the syringe for subsequent administration to a subject.

In yet another embodiment, the phospholipid is supplied as a dried film on the wall of a container, such as a syringe. A dried glycoprotein preparation, preferably in powdered form, then is sterilly introduced into the same container. Introducing a pharmaceutically acceptable carrier solution into the container and vortexing it produces the reconstituted membrane vesicle product of the invention. Alternatively, the glycoprotein can be in solution when introduced into the container.

In another embodiment, the product is supplied within a two compartment syringe, with dried phospholipids in one compartment, and glycoproteins in solution in another compartment. Such syringes are disclosed in U.S. Pat. Nos. 4,792,329 and 4,822,340, the disclosures of which are herein incorporated by reference. Depressing the syringe plunger forces glycoprotein solution into the phospholipid compartment. The syringe is vortexed for a recommended period of time, and the reconstituted platelet membrane vesicles can then be administered to the subject.

Another embodiment of the product has both the phospholipid and the glycoprotein conveniently supplied in a multicompartment container, such as a container adapted for use with an intravenous set. Such containers are disclosed in U.S. Pat. Nos. 4,548,023, 4,550,825, 4,731,053, and 4,994,056, the disclosures of which are herein incorporated by reference. The contents of the different compartments can be combined by puncturing or breaking dividers between the compartments. The glycoproteins, if in dried form, are rehydrated with sterile water or an isotonic salt solution, and the solution is then added to the phospholipid compartment. One preferred form of such a container would be a bag adapted for use with an intravenous infusion set.

The embodiments described above could each be conveniently supplied in kit form. Such kits might contain all the components required for sterile storage, reconstitution and use of the product at the site of actual administration to a treated subject. These kits might advantageously be supplied in a sterile covering holding all the supplies needed for use. The contained supplies might include the phospholipid preparation and the glycoprotein preparation in appropriate formulations and containers, solvent for reconstitution, syringes, needles, intravenous sets, or other supplies for administration to the subject, and directions for storage and use.

In any of the foregoing embodiments the various preparations can be supplied in amounts preselected to yield a therapeutically effective and appropriate dose of formed vessicles.

As mentioned above, the vesicles of this invention may be applied topically. Topical administration refers to application of the product to body surfaces, including the skin, mucous membranes, or surgically exposed surfaces of other body tissues or organs. A topical preparation may be useful for hemostasis during surgery on and around many body components, including the brain, the face during plastic surgery, musculoskeletal system, lungs, and abdominal organs. The preparation may be particularly useful in treating blood loss through the abraded or burned skin of trauma victims. Another indication for use of the product would be for controlling bleeding from small blood vessels in the nasal and sinus mucosa, as occurs in nose bleeds. The preparation may be used prophylactically in these and other circumstances.

In topical applications, a hemostatic effect is present when the topical preparation containing the vesicles of the invention demonstrates a measurable hemostatic effect as compared to the topical preparation without the vesicles.

Topical preparations in typical formulations include powders, lotions, gels, creams, ointments, foams, or solutions, as are known to those skilled in the art. Such formulations would include appropriate carriers, diluents, solvents, and vehicles, including water, saline, or polyols. These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. To achieve an isotonic solution, it may also be desirable to include agents such as sugars, sodium chloride, and the like. Other medically appropriate active ingredients might also be incorporated, including vasoconstrictors, growth factors, and local anesthetics.

The topical products might be supplied in appropriate containers. Depending on the use, these containers might include jars, bottles, tubes, or blister packs for single unit doses. Formulations for nasal treatment might preferably be supplied in either dropper bottles, or bottles with spray dispensers.

In an additional embodiment, the preparation could be provided incorporated into a bandage, swab, or dressing for application to bleeding body surfaces. Such a dressing may also encompass an absorbable gel or foam pad, which could be applied during surgery and allowed to remain in place in the body. A bandage could be manufactured with the reconstituted platelet membrane vesicles of the invention incorporated into a gel surface, which would contact the bleeding body surface of the subject to be treated.

EXAMPLES

Preparation of Platelet Glycoproteins

Platelet glycoproteins were prepared by modification of a procedure originally described by Wicki and Clemetson (1987). Outdated platelet concentrates were pooled and centrifuged at 350 g for 10 min to remove the red blood cells. The resultant platelet rich plasma was centrifuged again at 1500 g for 15 min to give a pellet containing platelets, which were suspended in 10 ml per original platelet unit in buffer A (4.8 mM glucose, 3 mM KCl, 100 mM NaCl, 10 mM EDTA, 30 mM sodium citrate, pH 6.5). This suspension was centrifuged at 1500 g for 15 min, and the resultant pellet was washed twice with buffer B (10 ml per original platelet unit; 30 mM glucose, 120 mM NaCl, 10 mM EDTA, 5 mM sodium citrate, pH 6.5) and once with buffer C (10 ml per original platelet unit; 134 mMNaCl, 10 mM EDTA, 10 mM Tris/HCl, pH 7.4). The platelet pellet than was solubilized in buffer D (124 mM NaCl, 20 mM EDTA, 2 mM phenylmethysulfonyl fluoride, 2 mM N-ethylmaleimide, 2% Triton X-114, 10 mM Tris/HCl, pH 7.4) with a volume equivalent to the pellet. The mixture was stirred at room temperature for 30 min and centrifuged at 2500 g for 2 hours at 4° C. The supernalant was further clarified by ultra-centrifugation at 100,000 g for 1 hour at 4° C. to give a clear solution for the following sucrose cushion centrifugations. Twenty ml aliquots of 6% sucrose in buffer E (154 mM NaCl, mM EDTA, 0.06% Triton X-114, 10 mM Tris/HCl, pH 7.4) were introduced into 50 ml centrifuge tubes and were warmed to 35° C. and carefully overlayered with 20 ml of clear supernatant from the ultracentrifugation. After spinning at 1000 g for 10 min at 30° C., the top layers of all the tubes were collected and enriched with additional 1% Triton X-114 (w/w). The solution, which turned cloudy after being warmed to 35° C., was again overlayered and centrifuged with 6% sucrose cushions as above. The top layers of all the tubes were collected (as 2nd SC Top) and contained platelet proteins.

The crude glycoproteins were further purified by affinity chromatography with wheat germ lectin (WGL)-Sephrose 4B which primarily interacts with several platelet glycoproteins such as GPIb, GPIa, and GPV (Clemetson et al., 1977). Fractions eluted from the WGL column were collected and monitored by dot assay using monoclonal antiglycocalicin (P6D9G) as primary antibody, and only those showing positive results were pooled, concentrated, dialyzed and filtered for further use.

Wheat germ lectin (WGL) Sephrose 4B (1.5 mg WGL/ml gel) was prepared from CNBr-activated Sephrose 4B according to the procedure from the manufacturer (Pharmacia). The solubilized platelet protein solution (50–80 ml of 2nd SC Top) was applied to a column of WGL-Sephrose 4B (2.5×8 cm) equilibrated in 20 mM Tris HCl, pH 7.4. After the flow through and extensive washing, the bound material was eluted with 2.5% N-acetylglucosamine in the same buffer. Fractions, which showed positive in dot assay using monoclonal antiglycocalicin as primary antibody, were pooled, concentrated with Amocon concentrators and further dialyzed against 20 mM Tris/HCl, pH 7.4. The monoclonal antiglycocalicin was made by standard methods as are well known to those skilled in the art. The purified glycoproteins were then filtered (0.2 um filter) and stored at −80° C.

The concentrated and dialyzed glycoproteins from the WGL affinity column may be further purified by anion exchange chromatography with a DEAE-Sepharcel column (2.5×27 cm) equilibrated with buffer F (30 mM NaCl, 20 mM MeS/HCl, pH 5.5). The column was eluted with a 200 ml gradient of 0.03–0.6 M NaCl in buffer F followed by 1M NaCl in buffer F. The fractions were collected and analyzed by $OD_{280}$ nm and dot assay. Those containing GPIb complex were pooled, concentrated, dialysed and filtered for further use.

Preparation of Platelet Membrane Lipid Extract

The platelet membrane lipids were extracted from platelet membranes. To produce platelet membranes, 600 ml of pooled platelet concentrates were centrifuged at 1,100 rpm for 11 minutes at 22° C. to remove contaminating red and white blood cells. The supernatant fluid portions, containing the platelets, were centrifuged at 3,000 rpm for 25 minutes at 22° C. to separate platelets from plasma. After discarding the platelet-poor plasma, the platelet pellets were resuspended in 20 ml of 0.9% saline, and diluted to a final volume of 100 ml. The resuspended platelets were pelletted again by centrifugation at 3,000 rpm for 20 minutes at 22° C. The wash was repeated twice more. After resuspension, the washed platelets were disrupted by repeated freezing (at −80° C. for at least six hours) and thawing (at 25° C. for at least one hour), three times. The frozen and thawed suspension was diluted with physiological saline (100 ml per each 600 ml unit) and centrifuged at 3,000 rpm for 30 minutes to collect a platelet ghost pellet. This platelet ghost pellet was resuspended in physiological saline (100 ml per each 600 ml unit) and washed twice by repeated centrifugation and resuspension.

Several of the examples below refer to the use of an Infusible Platelet Membrane (IPM) preparation as a membrane source in the experimental protocols. IPM is a preparation of isolated native platelet membranes, formed into microparticles. Phospholipid analysis shows that the phospholipid compositions of both native platelet membranes and of IPM are identical. To prepare IPM, the platelet membrane preparation of the preceding paragraph was heated and then sonicated according to the method as described in U.S. patent applications serial numbers 07/508,832 and 07/337,916.

Hexane/isopropanol mixture (HIP, 3:2 v/v) has been demonstrated as an effective solvent system for the extraction of phospholipids from cells and cell fractions (Saunders and Horrack, 1984). A mixture of 4 ml of IPM and 4 ml of HIP was vigorously mixed by vortex for 1 min in a screw-capped tube. A total of 80 ml of IPM in 20 tubes was processed. After the centrifugation (2500 g for 10 min) the top organic layer of each tube was collected as HIP/Top. The content of phospholipids was determined by HPLC and an aliquot of the lipid extract (HIP/Top) was dispensed into 15 ml tubes (each with 4 mg of phospholipids), capped tightly and stored at −80° C.

Preparation of Red Cell Membrane Lipid Extract

A similar HIP extract procedure as described above was employed to prepare the red cell membrane lipids. Red cells were isolated from anticoagulated whole blood by centrifugation. A red cell membrane solution was prepared from red cell ghost in the same manner as that of IPM including heating (60° C. for 20 hours) and sonication.

Preparation of Reconstituted Platelet Membranes Vesicles (RPMV) and Reconstituted Red Cell Membrane Vesicles (RRCMV)

After being warmed up to room temperature, the tubes containing platelet lipid extract were evaporated to dryness by a shaker/evaporator. The evaporation process was carried out under vacuum with shaking at 55°–60° C. to ensure a uniform lipid coating on the walls of the glass tubes. An aliquot of 3.65 ml of the protein solution prepared as described above (in 154 mM NaCl, 20 mM Tris/HCl, pH 7.4) was immediately added to the dry lipids and vigorously mixed by vortex for 3 min. The reconstituted membranes prepared as such appeared as a homogenous milky solution which can be stored at 4° C. for further use. This procedure was also employed for preparing the reconstituted red cell membranes except that the lipid extract was from red cells instead of platelets.

Determination of Protein, Cholesterol, and Phospholipids

Protein concentration was determined by the Lowry method (Lowry et al., 1951). In the case of glycoprotein solution in Tris/Hcl buffer, the protein concentration (in mg/ml) was estimated from the $OD_{280}$ nm reading divided by a factor of 1.3. Cholesterol was determined using an enzyme kit according to the procedure from the manufacturer (Sigma Chemical Company).

The content of five major phospholipids of the HIP extract was determined by the HPLC analysis modified from a reported procedure (Chen and Kou, 1982). HPLC analysis was carried out with a Waters Liquid Chromatographic system consisting of a Model 600E solvent delivery system, a Model U6K injector, a Model 481 variable wavelength detector, a Model 745 B integrator and a strip chart recorder. The column was a Zorbax Sil (25 cm×4.6 mm I.D., 5 um, DuPont) and eluted with a solvent of acetonitrile:methanol:85% phosphoric acid (250:12:3.3, v/v) at a flow rate of 1 ml/min. The dry HIP liquid samples were dissolved in an aliquot of chloroform:methanol (10:1) mixture for injection and the detection was recorded at 203 nm.

Platelet glycoproteins and reconstituted platelet membranes were also analysed by size exclusion HPLC. A column of TSK 5000pw (25 cm×4.6 mm I.d., 10 um, Beckman) was eluted with an isocratic mobile phase of 145 mM NaCl, 10 mM HEPES, pH 7.4. The flow rate was 1 ml/min and detection was at 280 nm.

Antibodies

Monoclonal antibody against purified human platelet glycocalicin (an anti GPIb antibody designated P6D9G) was developed by PRP, Inc., Watertown, Md. according to standard procedures. Monoclonal antibody against human platelet IIb/IIIa was obtained from Pel-Freeze (Brown Deer, Wis.). Polyclonal rabbit antibody was prepared against human platelet IIb/IIIa. Polyclonal antihuman serum albumin was purchased from Sigma Chemical Company (St. Louis, Mo.).

Polyacrylimide Gel Electrophoresis and Immunoblotting

One dimensional SDS-PAGE at reducing condition was performed in a 7.5% running gel as described by Davis (1964). Proteins were transferred from gels to nitrocellulose sheets (Schleicker and Schuell) by the method of Towbin et al. (1979). The binding of the primary antibody (P6D9G) against glycocalicin was detected with peroxidase-labeled second antibody using naphthol as substrate.

Dot Assay

The dot assay is a rapid and convenient method to identify the presence of certain proteins or antigens in given samples. Small aliquots (1-2 μl) of protein solution were applied to nitrocellulose sheets. After blocking the nonspecific sites, the sheets were incubated with primary and labeled secondary antibodies, followed by incubation with labeled peroxidase and naphthol as substrate for color development. Dark-colored dots indicate the presence of proteins or antigens binding with the primary antibody.

In the case of lipid/protein reconstitution, one ml of the reaction mixture obtained from the reconstitution process as above, was centrifuged at 14 Kg for 30 min. The pellets were washed 3-4 times with 154 mM NaCl, 20 mM Tris/HCl, pH 7.4 and resuspended in 0.5 ml. Samples of all the supernatants and pellets from each wash were analyzed by dot assay.

Results

Isolation of Human Platelet Glycoproteins

Figure 1:
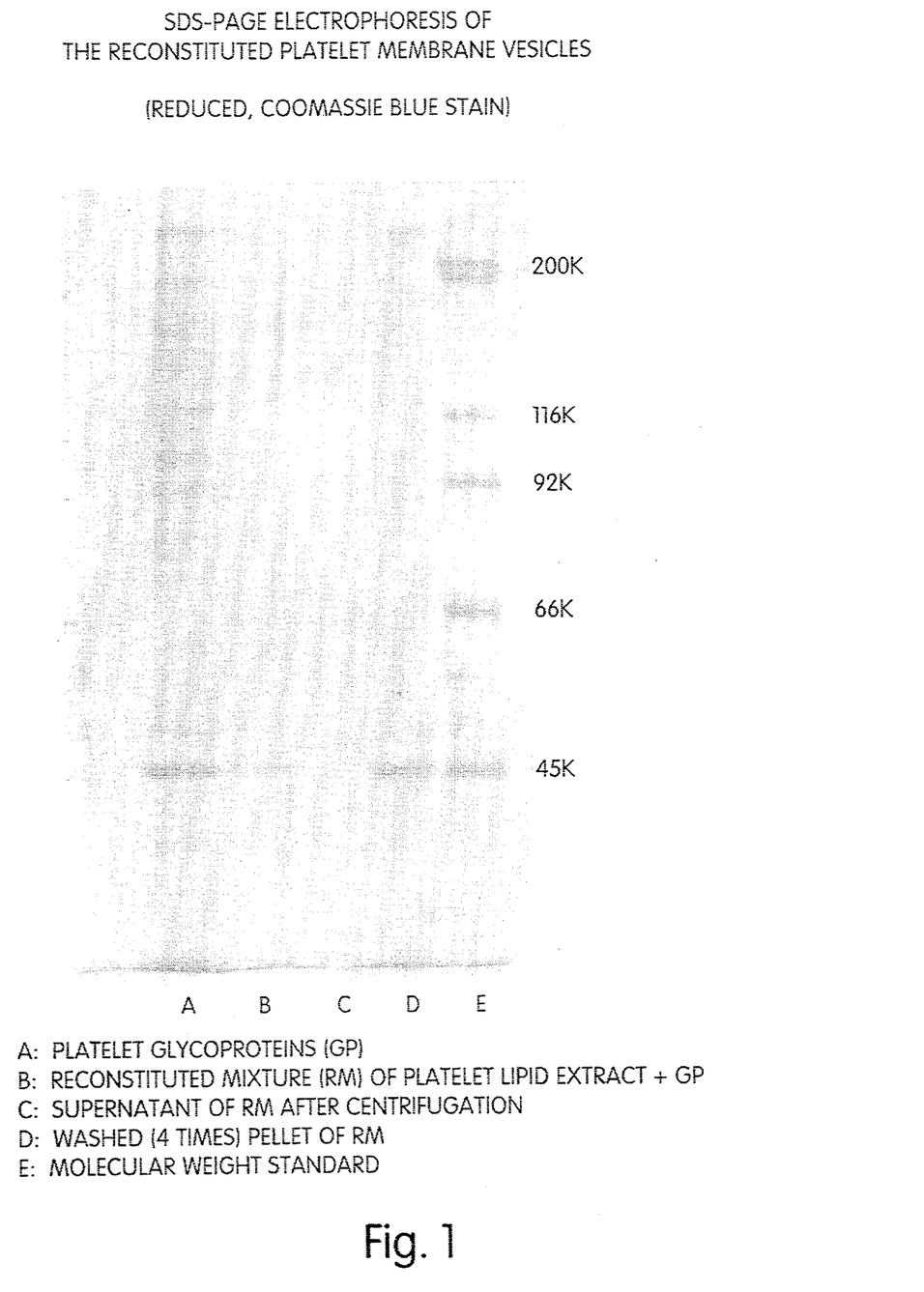
FIG. 1 depicts the results of SDS-PAGE electrophoresis of reconstituted platelet membrane vesicles.

Platelet glycoproteins purified by WGL-affinity chromatography showed several major bands in the SDS-PAGE gels under reducing condition and stained with Coomassie blue (FIG. 1, lane A). The lanes depicted were as follows:
A: Platelet glycoproteins (GP).
B: Reconstituted mixture (RM) of platelet lipid extract+GP
C: Supernatant of RM after centrifugation
D: Washed (4 times) pellet of RM
Molecular weight standard According to Wicki and Clemetson, one of the high molecular weight bands (200 KDa) is actin-binding protein. The poorly stained band around 145 KDa is GPIb-alpha. Bands between 90-120 KDa are the degraded GPIb, IIb, or IIIa. The 45 KDa band is combined of actin and a fragment of GPIb-alpha. Glycoproteins further purified with DEAE-Sepharcel chromatography did not show any reduction of bands in SDS-PAGE (results are not shown).

Figure 2:
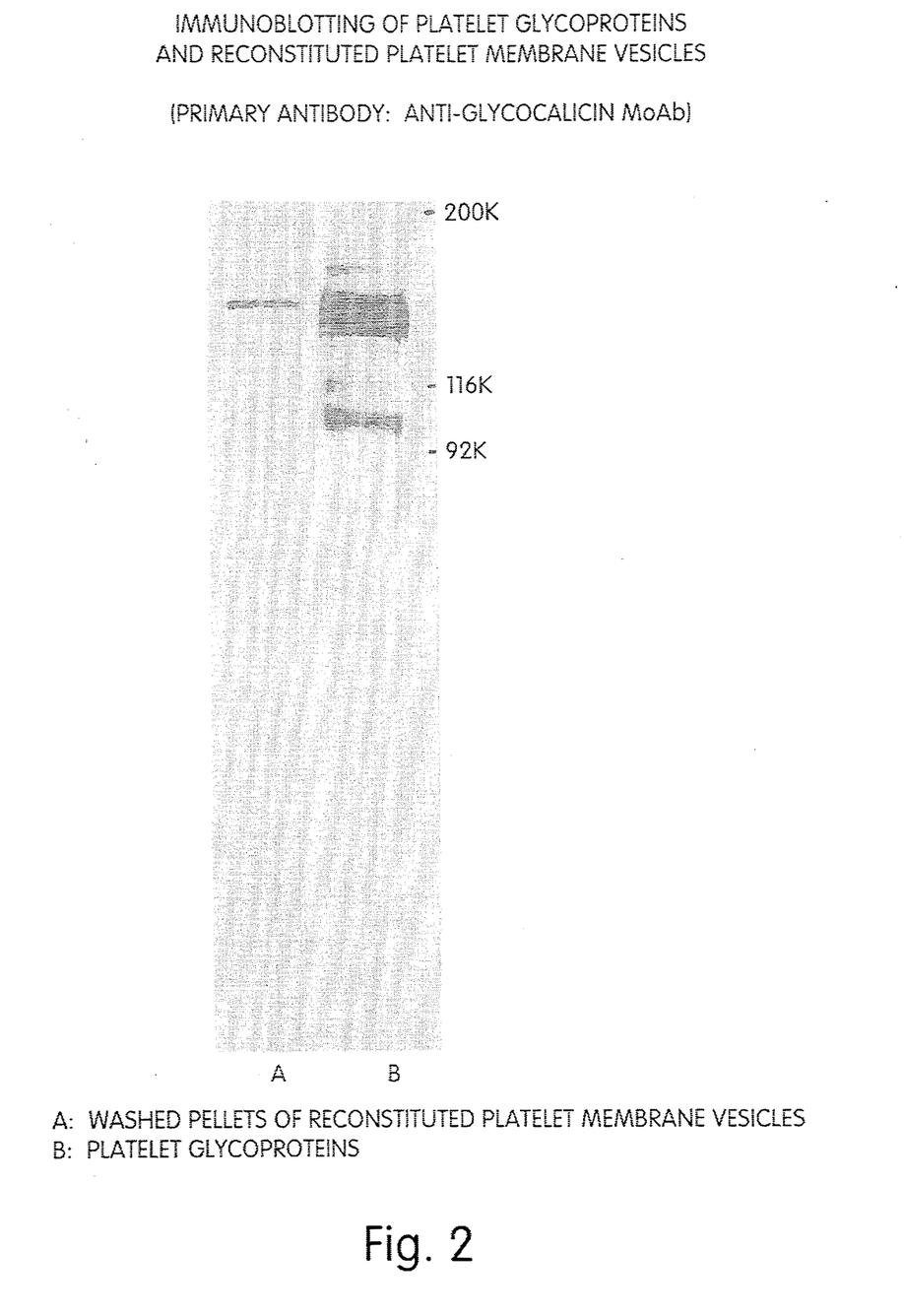
FIG. 2 is an immunoblot of platelet glycoproteins and reconstituted platelet membrane vesicles.

FIG. 2 depicts an immunoblot corresponding to a gel containing washed, reconstituted platelet membrane vesicles (lane A) and platelet glycoproteins (lane B). Among all the electrophoretic fragments (reducing conditions), a broad band of 145 KDa is the major component responsible for the binding of monoclonal antiglycocalicin in the immunoblotting (FIG. 2, lane B).

Figure 3:
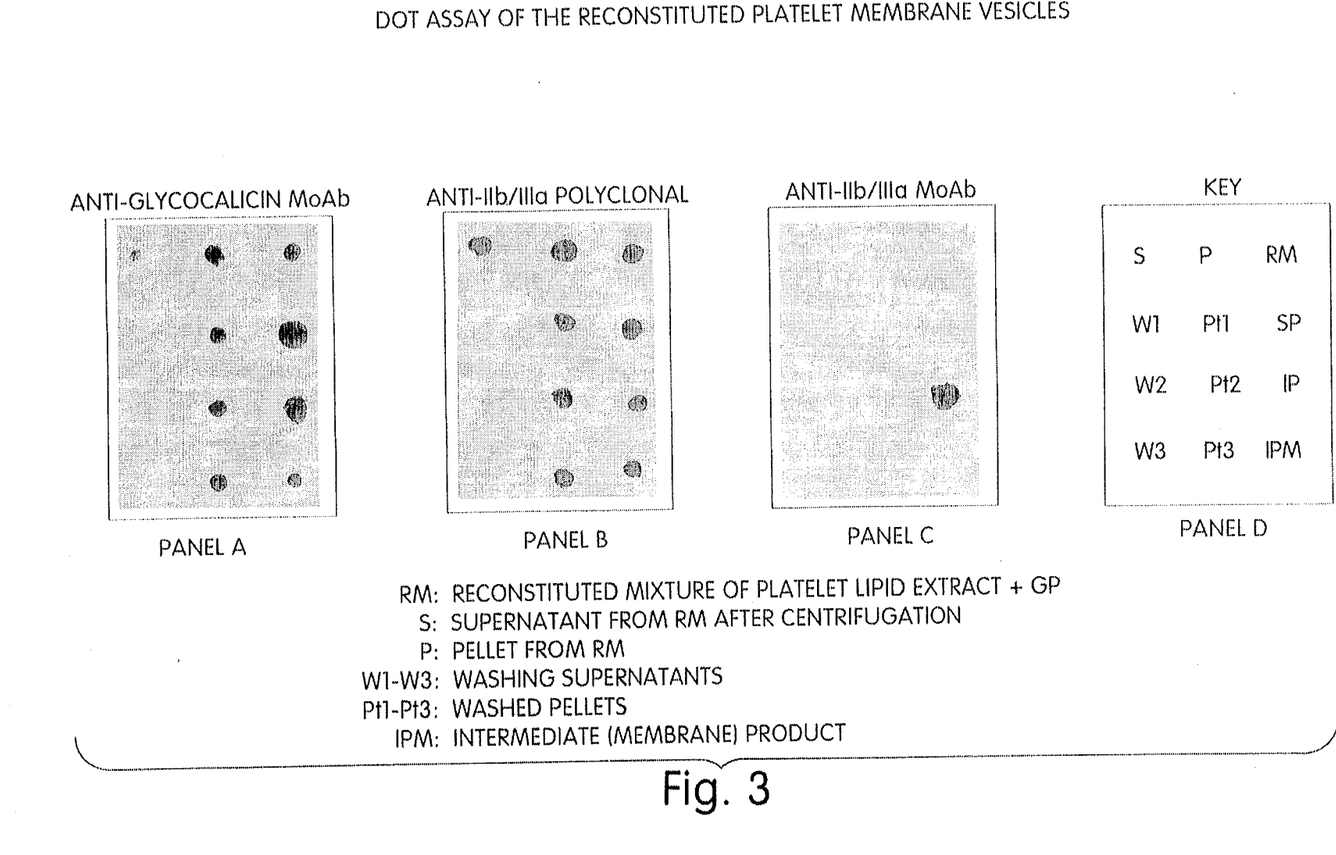
FIG. 3 is a immunological dot assay of reconstituted platelet membrane vesicles.

Incorporation of Glycoproteins into Reconstituted Platelet Membrane Vesicles Using the hydration procedure described above, it is found that GPIb and other platelet glycoproteins can be incorporated into platelet membrane vesicles (PMV). FIG. 3 depicts the identification of platelet glycoproteins of reconstituted platelet membrane vesicles by an immunological dot assay. In Panel A, the primary antibody used is a monoclonal antibody against platelet glycoprotein Ib (P6D9G). Panels B and C respectively use polyclonal and monoclonal antibody against platelet GP IIb/IIIa as primary antibody. The code for the samples applied on the nitrocellulose sheet shown in panels A-C is as follows: RM is the reconstituted mixture of platelet lipid and glycoprotein; S is the supernatant fluid from RM after centrifugation; P is the pellet from RM; W1-3 indicates one of three different washing supernatants; Pt1-3 each shows one of three different washed pellets; and IP is the intermediate membrane product without heat treatment. The position of each sample is shown in Panel D.

The result of a dot assay on the reconstituted PMV using P6D9G as the primary antibody showed no loss of GPIb in the pellets after 3 (or 4) times of washing with 154 mMNaCl, 20 mM Tris/HCl, pH 7.4 (Panel A; Pt1-3). The presence of GPIIb and GPIIIa in the reconstituted PMV is also evident as shown in the result of the dot assay using a polyclonal anti-GPIIb/IIIa as the primary antibody (Panel B). However, no GPIIb/IIIa complexes were detected in the purified glycoproteins, reconstituted mixture and all the washed pellets as shown in Panel C. Only the non heat-treated platelet membranes bound to the specific monoclonal antibody against GPIIb/IIIa complex.

SDS-PAGE gels also demonstrated that glycoproteins were incorporated into the reconstituted PMV.

The repeatedly washed pellets (FIG. 1, lane D) retained all the bands of purified glycoproteins (FIG. 1, lane A). Immunoblotting of washed pellets of reconstituted PMV showed a prominent band at 145 KDa as an indication of the presence of GPIb (FIG. 2, lane A).

Figure 4:
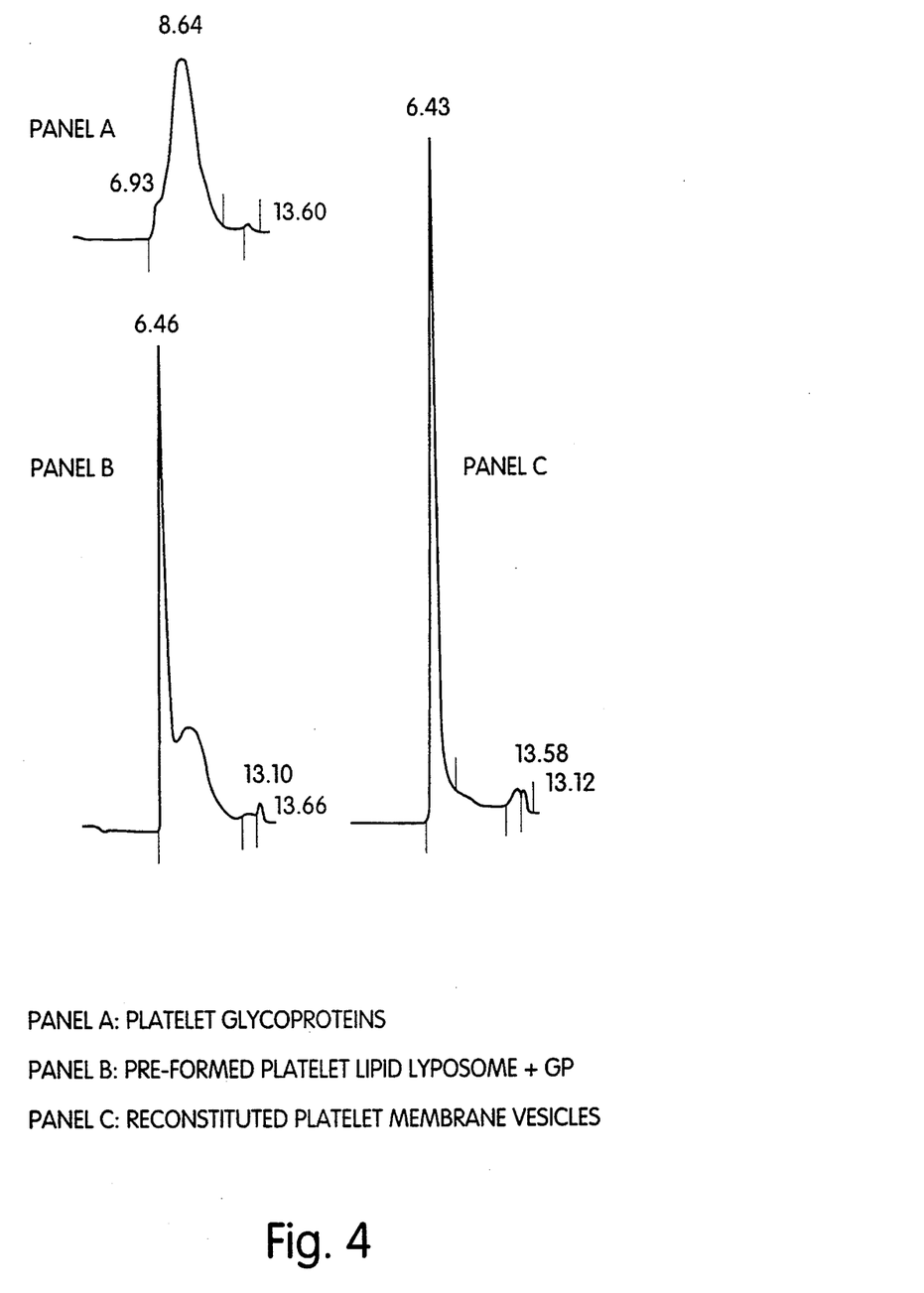
FIG. 4 is a high performance liquid chromatograph of purified platelet glycoproteins and of reconstituted platelet membrane vesicles.

The incorporation of purified glycoproteins into reconstituted PMV is again revealed in the size exclusion HPLC chromatogram. FIG. 4 depicts size-exclusive HPLC analysis of purified platelet glycoproteins and reconstituted membrane preparations. For these measurements, the HPLC analysis conditions were: column TSK 5000PW (75 cm×4.6 mm, 10 um, Beckman Instruments); isocrated mobile phase: 145 mM NaCl, 10 mM HEPES, pH 7.4; flow rate 1 ml/min; detection wavelength 280 nm. The chromatogram of FIG. 4, Panel A shows the purified platelet membrane glycoproteins. The chromatogram of Panel B depicts the mixture of platelet membrane glycoproteins and a liposome suspension previously prepared from hydrated and sonicated platelet membrane lipids in saline. The chromatogram of Panel C shows the reconstituted platelet membrane vesicles prepared from platelet membrane glycoproteins and lipid, demonstrating association of the glycoproteins with the phospholipids. Panel C shows the peak of glycoproteins (Rt=8.64 min) diminished and merged into the peak of the reconstituted PMV (Rt=4.63 min). However, the glycoproteins remained visible (Panel B) if they were directly added to a liposome solution previously prepared from hydrated and sonicated platelet membrane lipids in saline.

The reconstituted platelet membrane vesicles had enriched glycoprotein:phospholipid ratios estimated to be from about 3:10 to 6:10 and GPIb:phospholipid ratios from about 1:50 to 1:25. About 15% of the lipid starting materials was incorporated into the microvesicles, while more than 85% of the glycoproteins GPIb, GPIIb and GPIIIa were incorporated.

Figure 5:
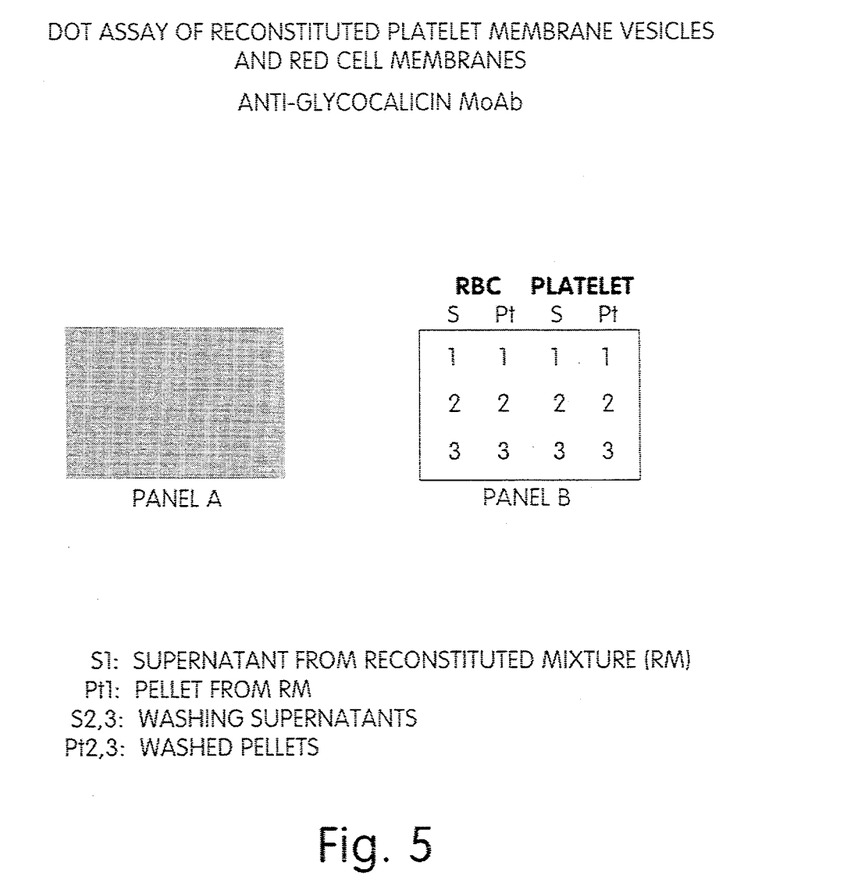
FIG. 5 is an immunological dot assay for glycoprotein Ib, comparing incorporation of the glycoprotein in vesicles formed with phospholipids from either platelet membranes or from red blood cell membranes.

The Specificity of Incorporation Between Human Platelet Lipids and Glycoproteins The specificity of incorporation between human platelet lipids and glycoproteins can be demonstrated by comparing the incorporation of purified platelet glycoproteins into membrane vesicles, where the vesicles are formed from either human platelet membrane lipids or red cell membrane lipids. The color intensity of pellets in the dot assay (FIG. 5) shows that the incorporation of GPIb into human platelet membrane lipids is greater than that into an equal amount of phospholipids from red cell membranes. This indicates that platelet glycoproteins have higher affinity for platelet membrane lipids than for red cell membrane lipids. Specifically, Panel A identifies platelet glycoprotein Ib in reconstituted membrane preparations by immunological dot assay. The preparations are reconstituted from platelet glycoproteins with either platelet phospholipids or red cell membrane phospholipids. The primary antibody used was P6D9G. The samples are labeled as follows: S1 is supernatant from the reconstituted mixture; Pt 1 is the pellet from the RM; S 2 and 3 are washing supernatants; and Pt 2 and 3 are washed pellets. The position of the samples is shown in Panel B.

Effect of Reconstituted Platelet Membrane Vesicles on Bleeding Time

Bleeding time was used to assess the hemostatic efficacy of platelet lyposomes, platelet glycoprotein complexes and reconstituted platelet membrane preparations. This involved the standard template bleeding time, performed in thrombocytopenic rabbits. In this test, a template is used to guide a shallow incision, one mm deep and 0.7 cm long. The blood lost through the cut is absorbed on a piece of filter paper. More specifically, RPMV solution was infused through marginal ear veins to non-anesthetized thrombocytopenic rabbits (platelet count <20,000/ml). Template bleeding time was determined before and at various intervals after infusion. For bleeding time measurements, the non-infused rabbit ear was supported on a smooth surface without pressure applied. A standardized incision was made with a commercial bleeding time device (Simplate, Organon Teknika of Durham, N.C.). The bleeding time was measured to the nearest 30 seconds using a filter paper intermittently applied to blot the blood drop. Although bleeding often exceeded 15 minutes, measurements were carried out only to 10 minutes to avoid excessive blood loss. In cases where the bleeding time exceeded 10 minutes, a value of 10 minutes was used in subsequent calculations.

The results from end point determination of bleeding time are shown in Tables 1–3. Post-infusion shortening of prolonged bleeding time was demonstrated only in thrombocytopenic rabbits receiving reconstituted platelet membrane preparations (Table 1). No effect was noted in animals receiving platelet lyposomes (Table 2) or platelet glycoproteins (Table 3). Results presented in Table 1 are divided into two groups: the top panel consisted of two animals, one of which (#82) received repeated infusions on two consecutive days; platelet counts for both animals on the day of infusion experiments were above 25,000/ul. On the other hand, platelet counts were below 15,000/ul for the other group (lower panel) on the day of infusion.

TABLE 1

Infusion Efficacy of Reconstituted Platelet Membrane Preparations

| Animal # | Platelet Count × 1000/ul | Bleeding Time (minutes) Post Infusion Interval (minutes) | | | |
|---|---|---|---|---|---|
| | | t0 | t20 | t120 | t240 |
| 77 | 53 | 8.5 | 7.0 | 5.0 | 5.5 |
| 82 | 40 | 7.5 | 6.0 | 5.0 | 6.5 |
| 82 | 30 | 8.0 | 5.0 | 5.0 | 6.0 |
| Mean ± SD (n = 3) | 41 ± 11.5 | 8.0 ± 0.5 | 6.0 ± 1.0 | 5.0 ± 0 | 6.0 ± 0.5 |
| 79 | 5 | >10 | 10.0 | >10 | >10 |
| 81 | 11 | 9.5 | 6.0 | 5.5 | 8.0 |
| 81 | 8 | >10 | 7.0 | 8.0 | 8.5 |
| 84 | 9 | >10 | 7.0 | 7.5 | 8.5 |
| 86 | 11 | >10 | 9.0 | 8.5 | 9.5 |
| 99* | 5 | >10 | 7.5 | 8.0 | 6.0 |
| 100* | 4 | 8.5 | 5.0 | 5.0 | 6.0 |
| Mean ± SD (n = 7) | 7.6 ± 2.9 | 9.7 ± 0.6 | 7.4 ± 1.7 | 7.5 ± 1.7 | 8.1 ± 1.6 |

*Further separation with DEAE-Sepharcel anion exchange chromatography

TABLE 2

Infusion Efficacy of Liposomes Formed from Platelet Membrane Extract

| Animal # | Platelet Count × 1000/ul | Bleeding Time (minutes) Post Infusion Interval (minutes) | | | |
|---|---|---|---|---|---|
| | | t0 | t20 | t120 | t240 |
| 41 | 8 | >10 | >10 | >10 | >10 |
| 42 | 16 | >10 | >10 | 6.5 | >10 |
| 44 | 6 | >10 | >10 | >10 | >10 |
| 45 | 12 | >10 | >10 | >10 | >10 |
| 83 | 8 | >10 | >10 | >10 | >10 |
| 87 | 14 | >10 | 7.5 | 7.5 | 9.0 |

TABLE 2-continued

Infusion Efficacy of Liposomes
Formed from Platelet Membrane Extract

| Animal # | Platelet Count × 1000/ul | Bleeding Time (minutes) Post Infusion Interval (minutes) | | | |
|---|---|---|---|---|---|
| | | t0 | t20 | t120 | t240 |
| 89 | 10 | >10 | >10 | >10 | >10 |
| 90 | 5 | >10 | >10 | >10 | 9.0 |
| 98 | 10 | >10 | >10 | >10 | >10 |
| Mean ± SD (n = 9) | 9.9 ± 3.6 | 10 ± 0 | 9.7 ± 0.8 | 9.3 ± 1.4 | 9.8 ± 0.4 |

TABLE 3

Infusion Efficacy of Platelet Glycoproteins

| Animal # | Platelet Count × 1000/ul | Bleeding Time (minutes) Post Infusion Interval (minutes) | | | |
|---|---|---|---|---|---|
| | | t0 | t20 | t120 | t240 |
| 85 | 6 | >10 | 8.5 | >10 | >10 |
| 87 | 8 | >10 | >10 | >10 | >10 |
| 98 | 10 | >10 | >10 | >10 | >10 |
| 99 | 5 | >10 | 9.5 | >10 | >10 |
| 100 | 4 | 9.0 | >10 | 8.0 | 9.0 |
| Mean ± SD (n = 5) | 6.6 ± 2.4 | 9.8 ± 0.5 | 9.6 ± 0.7 | 9.6 ± 0.9 | 9.8 ± 0.5 |

Effect of Reconstituted Platelet Membrane Vesicles on Blood Loss

The beneficial effect of the preparation was also evident using another measurement of hemostatic function, the blood loss through the standard incision described above. A copy of the filter paper used for bleeding time blots was made, blots were cut off and weighed. The cumulative weight for all blots obtained for each post-infusion intervals was compared to the control obtained before infusion of the test material (t=0).

Hemostatic efficacy was demonstrated by a reduction of blood loss, expressed by a decrease in the comparative percent of combined weight relative to the control considered as 100%. Results from the second method of measurement, summarized in Tables 4–6, confirmed the hemostatic efficacy of reconstituted platelet membrane preparations (Table 4). Also consistent with the results from end point determination (Tables 2 and 3), assessment of blood loss failed to show hemostatic effect of platelet lyposomes and platelet glycoproteins (Tables 5 and 6). Table 7 shows the lack of efficacy of a preparation of reconstituted red blood cell membranes.

TABLE 4

HEMOSTATIC EFFECT OF RECONSTITUTED PLATELET MEMBRANE PREPARATION

| Animal # | Combined weight of blots at t0 (mg) | Comparative percent of combined weight Post Infusion Interval (minutes) | | | |
|---|---|---|---|---|---|
| | | t0 | t20 | t120 | t240 |
| 86 | 90.8 | 100 | 15.0 | 12.6 | 24.2 |
| 79 | 275.3 | 100 | 15.8 | 9.2 | 24.2 |
| 77 | 35.8 | 100 | 24.0 | 14.5 | 34.9 |
| 81 | 164.7 | 100 | 4.6 | 5.7 | 14.5 |
| 81 | 42.7 | 100 | 28.8 | 32.1 | 41.9 |
| 82 | 32.3 | 100 | 22.9 | 9.0 | 99.4 |
| 82 | 11.4 | 100 | 23.6 | 93.0 | 192.1 |
| 99 | 151.2 | 100 | 3.2 | 17.0 | 3.8 |
| 100 | 38.8 | 100 | 12.9 | 15.2 | 38.1 |
| 84 | 25.3 | 100 | 12.3 | 56.9 | 132.8 |

TABLE 5

HEMOSTATIC EFFECT OF LIPOSOME

| Animal # | Combined weight of blots at t0 (mg) | Comparative percent of combined weight Post Infusion Interval (minutes) | | | |
|---|---|---|---|---|---|
| | | t0 | t20 | t120 | t240 |
| 83 | 62.2 | 100 | 317.8 | 50.8 | 440.4 |
| 90 | 123.5 | 100 | 68.9 | 171.5 | 39.4 |
| 98 | 292.8 | 100 | 33.2 | 114.2 | 13.1 |
| 89 | 111.8 | 100 | 111.9 | 155.3 | 69.0 |
| 87 | 118.4 | 100 | 9.6 | 6.8 | 13.6 |

TABLE 6

HEMOSTATIC EFFECT OF PLATELET GLYCOPROTEINS

| Animal # | Combined weight of blots at t0 (mg) | Comparative percent of combined weight Post Infusion Interval (minutes) | | | |
|---|---|---|---|---|---|
| | | t0 | t20 | t120 | t240 |
| 99 | 34.2 | 100 | 47.7 | 178.4 | 91.5 |
| 100 | 66.5 | 100 | 62.2 | 24.1 | 19.3 |
| 98 | 307.0 | 100 | 11.7 | 128.7 | 24.5 |
| 85 | 206.3 | 100 | 9.4 | 172.6 | 62.6 |
| 87 | 99.1 | 100 | 84.9 | 21.8 | 45.0 |

TABLE 7

INFUSTION EFFICACY OF RED CELL MEMBRANE PREPARATION

| Animal # | Dose: mg protein/ kg bw | Platelet Count × 1000/ul | Bleeding Time (minutes) Post Infusion Interval (minutes) | | | |
|---|---|---|---|---|---|---|
| | | | t0 | t20 | t120 | t240 |
| RM 1 | 5.2 | <9 | >10 | >10 | >10 | 8.0 |
| | 2.4 | <9 | >10 | >10 | 8.5 | 7.5 |
| RM 3 | 2.4 | 21 | >10 | >10 | >10 | 6.0 |
| | 5.2 | <21 | >10 | >10 | >10 | >10 |
| Mean ± SD (n = 4) | | 15 ± 6.9 | 10 ± 0 | 10.0 | 9.6 ± 0.8 | 7.9 ± 1.7 |

References

Baldasarre, J. J., Kahn, R. A., Knipp, M. A., and Newman, P. J. 1985. Reconstitution of platelet proteins into phospholipid vesicles. J. Clin. Invest. 75:35–39.

Chen SS, Kou AY: Improved Procedure for the Separation of Phospholipids by High-Performance Liquid Chromatography. J . Chromat. 227:25–31 (1982)

Clemetson KJ, Pfueller SL, Luscher EF, Jenkins CSP: Isolation of the Membrane Glycoproteins of HLLman Blood Platelets by Lectin Affinity Chromatography. Biochim Biophy Acta 464:493–508 (1977)

Davis BJ: Disc Electrophoresis-II: Method and Application to Human Serum Proteins. Ann NY Acad. Sci. 121:404–427 (1964)

Lowry OH, Rosebrough NJ, Farr AL, Randall RJ: Protein Measurement with Folin Phenol Reagent. J. Biol. Chem. 193:265–272 (1951)

Parise, L. V., and Phillips, D. R. 1985. Platelet membrane glycoprotein IIb-IIIa complex incorporated into phospholipid vesicles. J. Biol. Chem. 260:1750–1756.

Rybak, M. E., and Renzulli, Lo Nov. 15, 1990. A liposome based platelet substitute, the plateletsome, with hemostatic efficacy. Blood 76(10), Suppl 1:473a.

Rybak, M. E., Renzulli, L. A., Bruns, M. J., and Cahaly, D. P. 1988. Platelet glycoprotein IIb and IIIa as a calcium channel in liposomes. Blood 72:714–720.

Saunders RD, Horrocks LA: Simultaneous Extraction and Preparation for High Performance Liquid Chromatography of Prostaglandins and Phospholipids. Anal. Biochem 143:71–75 (1984)

Sie, P., Gillois, M., Boneu, B., Chap,. H., Bierme, R., and Douste-Blaze, L. 1980. Reconstitution of liposomes bearing platelet receptors for human yon Willebrand factor. Blochem. Biophys. Acta 97:133–138.

Towbin H, Staehelin T, Gordin J: Electrophoretic Transfer of Proteins from Polyacrylamide Gels to Nitrocellulose Sheets. Proc. Natl. Acad. Sci. USA 70:4350–4354 (1979)

Wicki AN, Clemetson KJ: The Glycoprotein Ib Complex of Human Blood Platelets. Eur. J. Biochem 163:43–50 (1987)

We claim:

1. A therapeutic composition comprising a pharmaceutically acceptable sterile preparation of micellar structures capable of promoting hemostasis, the micellar structures consisting essentially of a combination of glycoprotein and phospholipid.

2. The therapeutic composition of claim 1 wherein the glycoprotein:phospholipid ratio is between 1:20 and 3:5.

3. The therapeutic composition of claim 2 wherein the ratio is about 1:10.

4. The therapeutic composition of claim 1 wherein the glycoprotein comprises glycoprotein Ib and wherein the glycoprotein Ib:phospholipid ratio is between 1:50 and 3:5.

5. The therapeutic composition of claim 4 wherein the ratio is between 1:25 and 1:10.

6. The therapeutic composition of claim 1 wherein the glycoprotein comprises glycoprotein Ib and wherein the glycoprotein Ib: phospholipid ratio is about 1:10.

7. The therapeutic composition of claim 1 wherein the composition is free of glycoprotein IIb/glycoprotein IIIa complex.

8. The therapeutic composition of claim 1 wherein the lipid composition permits greater than 80% incorporation of the glycoprotein when the glycoprotein:phospholipid ratio as starting materials is about 1:10.

9. The therapeutic composition of claim 8 wherein the glycoprotein is glycoprotein Ib.

10. The therapeutic composition of claim 8 wherein the glycoprotein is glycoprotein IIb or glycoprotein IIIa.

11. The therapeutic composition of claim 1 wherein the micellar structures are formed of a phospholipid having procoagulant activity.

12. The therapeutic composition of claim 1 wherein the micellar structures are derived from non-human platelets and human platelets.

13. The therapeutic composition of claim 1 further comprising a therapeutic agent entrapped within the lumina of the micellar structures or incorporated in the micellar structure membrane.

14. The therapeutic composition of claim 1,2,3,4,5,6,7,8 or 11 wherein the material is formulated in an in vivo pharmaceutically effective preparation.

15. The therapeutic composition of claim 14 wherein the preparation comprises a bactericidal agent.

16. A pharmaceutical preparation comprising a pharmaceutically acceptable sterile preparation of micellar structures capable of promoting hemostasis, wherein the preparation is in a spray-bottle container.

* * * * *